United States Patent
van Ginkel et al.

(10) Patent No.: US 8,889,636 B2
(45) Date of Patent: Nov. 18, 2014

(54) ANTI-MICROBIAL COMPOSITIONS

(75) Inventors: Roel van Ginkel, Nelson (NZ); Andrew Ian Selwood, Nelson (NZ); Alistair Lawrence Wilkins, Hamilton (NZ); Stephen Ford, Franklin (NZ); Cody Calder, Franklin (NZ)

(73) Assignee: Biotelliga Holdings Limited, Auckland (NZ)

( * ) Notice: Subject to any disclaimer, the term of this patent is extended or adjusted under 35 U.S.C. 154(b) by 125 days.

(21) Appl. No.: 13/216,443

(22) Filed: Aug. 24, 2011

(65) Prior Publication Data

US 2012/0108526 A1 May 3, 2012

Related U.S. Application Data

(60) Provisional application No. 61/376,402, filed on Aug. 27, 2010.

(51) Int. Cl.
| | | |
|---|---|---|
| *A61K 31/70* | (2006.01) | |
| *A61K 31/35* | (2006.01) | |
| *A01N 49/00* | (2006.01) | |
| *C07D 493/04* | (2006.01) | |
| *A01N 63/04* | (2006.01) | |
| *C07H 1/00* | (2006.01) | |

(52) U.S. Cl.
CPC C07H 1/00 (2013.01); A01N 49/00 (2013.01); C07D 493/04 (2013.01); A01N 63/04 (2013.01)
USPC ............................................. 514/23; 514/456

(58) Field of Classification Search
None
See application file for complete search history.

(56) References Cited

FOREIGN PATENT DOCUMENTS

JP        2002/047281      *   2/2002

OTHER PUBLICATIONS

Wolff, Manfred E., "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Bhuiyan, S.A., et al., Evaluation of potential biocontrol agents against *Claviceps africana* in vitro and in vivo, Plant Pathology (2003) 52, 60-67.
Brown, Averil E., et al., Antifungal Compounds produced by *Epicoccum purpurascens* Against Soil-Borne Plant Pathogenic Fungi, Soil Biol. Biochem. vol. 19, pp. 657-664, 1987.
Burge, William R., et al., Isolation and Biological Activity of the Pigments of the Mold *Epicoccum nigrum*, J. Agric. Food Chem., vol. 24, No. 3, 1976, pp. 555-559.
Erlangung, Zur, Isolation, Structure Elucidation and Evaluation of Anti-inflammatory and Anti-infectious Activities of Fungal Metabolites, Dissertation, Aug. 11, 1973, Bangoua, 134 pgs.
Frederick, Clay B., et al., Structure of Triornicin, a New Siderophore Biochemistry 1981, 20, 2436-2438.
Wangun, Hilaire F. Kemami, et al., Epicoccamides B-D, Glycosylated Tetramic Acid Derivatives from an *Epicoccum* sp. Associated with the Tree Fungus *Pholiota squarrosa*, J. Nat. Prod. 2007, 70, 1800-1803.
Mari, Marta, et al., control of post-harvest brown rot on nectarine by *Epicoccum nigrum* and physico-chemical treatments, J. Sci. Food Agric. 87, 1271-1277 (2007).
Shu, Yue-Zhong, et al., Orevactaene, A Novel Binding Inhibitor of HIV-1 rev Protein to Rev Response Element (RRE) From *Epicoccum nigrum* WC47880, Bioorganic & Medicinal Chemistry Letters, vol. 7, No. 17, pp. 2295-2298, 1997.
Szandala, E.S and Backhouse, D., Suppression of sporulation of *Botrytis cinerea* by antagonists applied after infection, Australasian Plant Pathology, 2001, 30, 165-170.
Wright, Anthony D., et al., Epicoccamide, a novel secondary metabolite from a jellyfish-derived culture of *Epicoccum purpurascens*, Org. Biomol. Chem., 2003, 1, 507-510.

* cited by examiner

*Primary Examiner* — Traviss C McIntosh, III
(74) *Attorney, Agent, or Firm* — King & Schickli, PLLC

(57) ABSTRACT

Antimicrobial compounds from *Epicoccum purpurascens* (syn. *E. negrum*) for use against plant and fungi pathogens. An orange yellow metabolite was isolated, the structure elucidated as a small group of compounds Epipyrone A-C and fungicidal activity demonstrated against plant pathogens, for example *Botrytis cinerea* and *Lecanicillium muscarium*. Agricultural and pharmaceutical compositions are provided, and use thereof in treating microbial infections in an animal or plant are also provided.

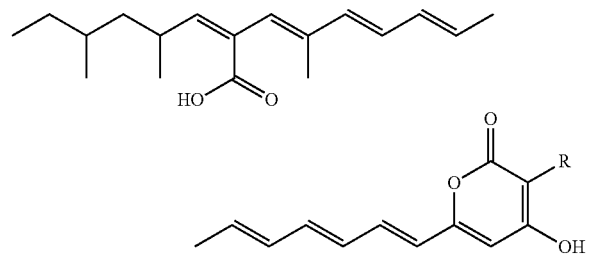

11 Claims, 13 Drawing Sheets

A
B
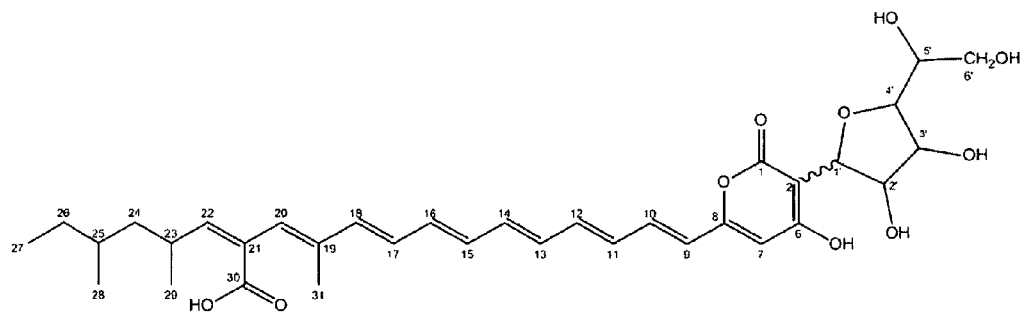
FIGURE 2A,B

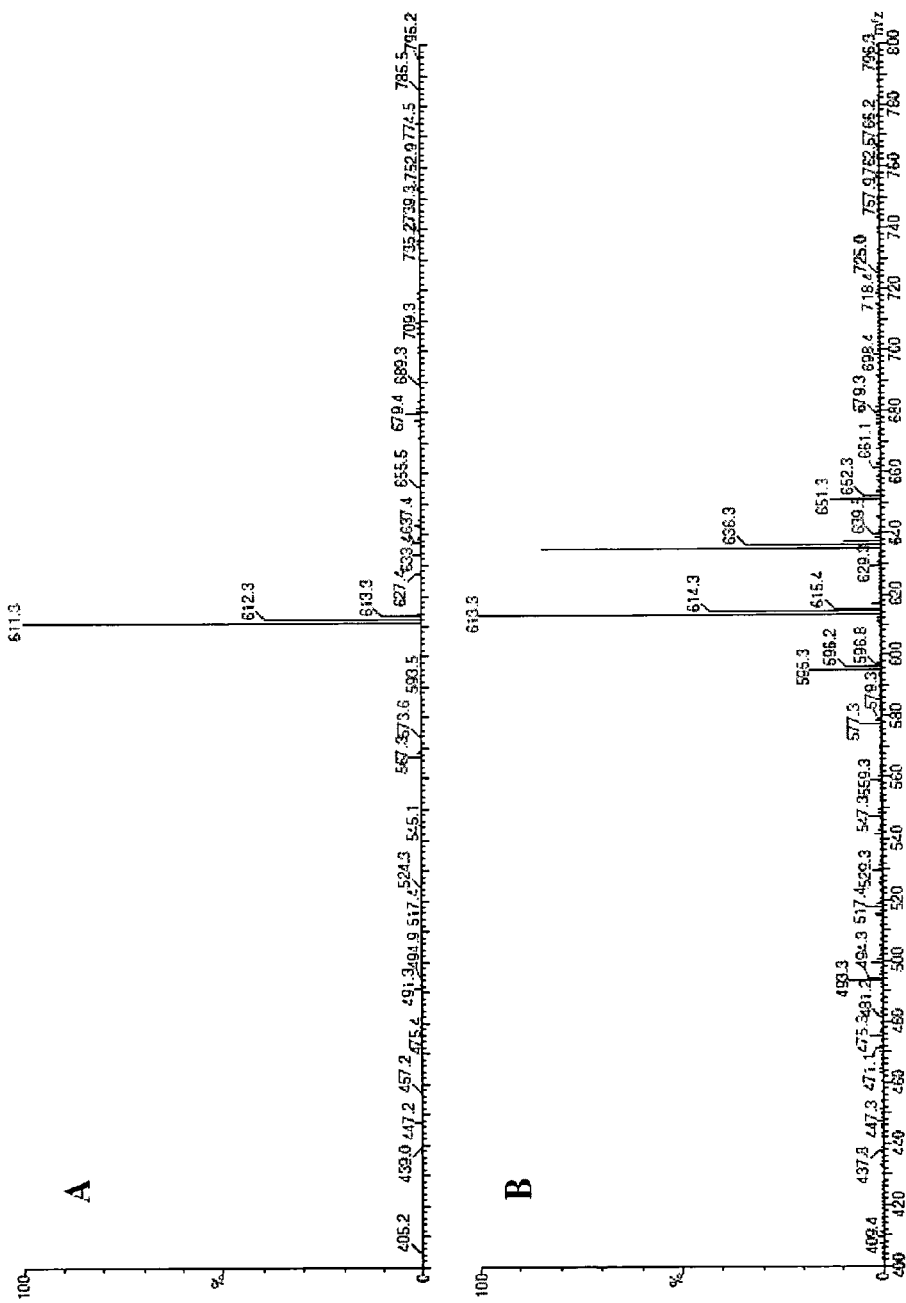
FIGURE 3A,B

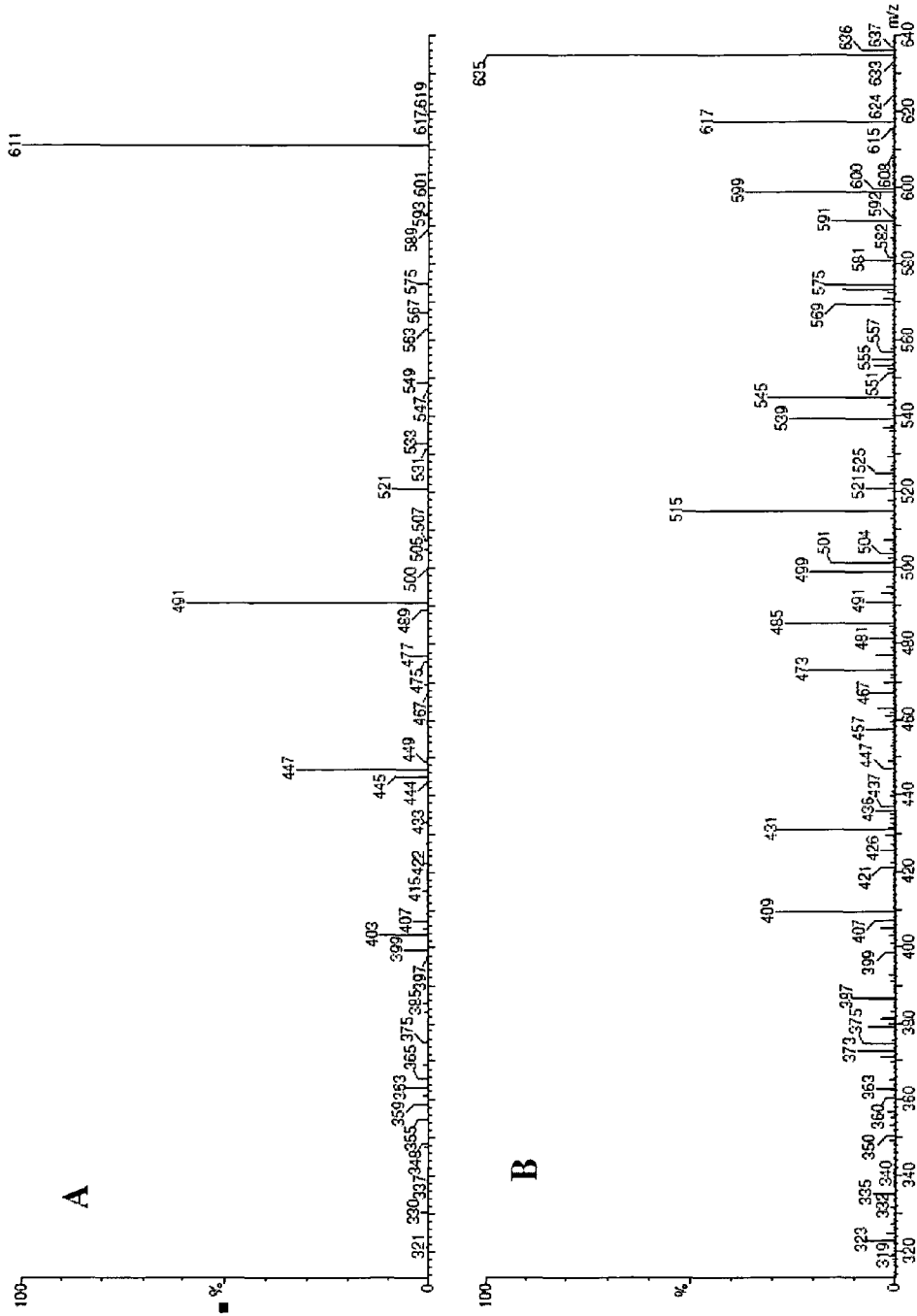
FIGURE 4A,B

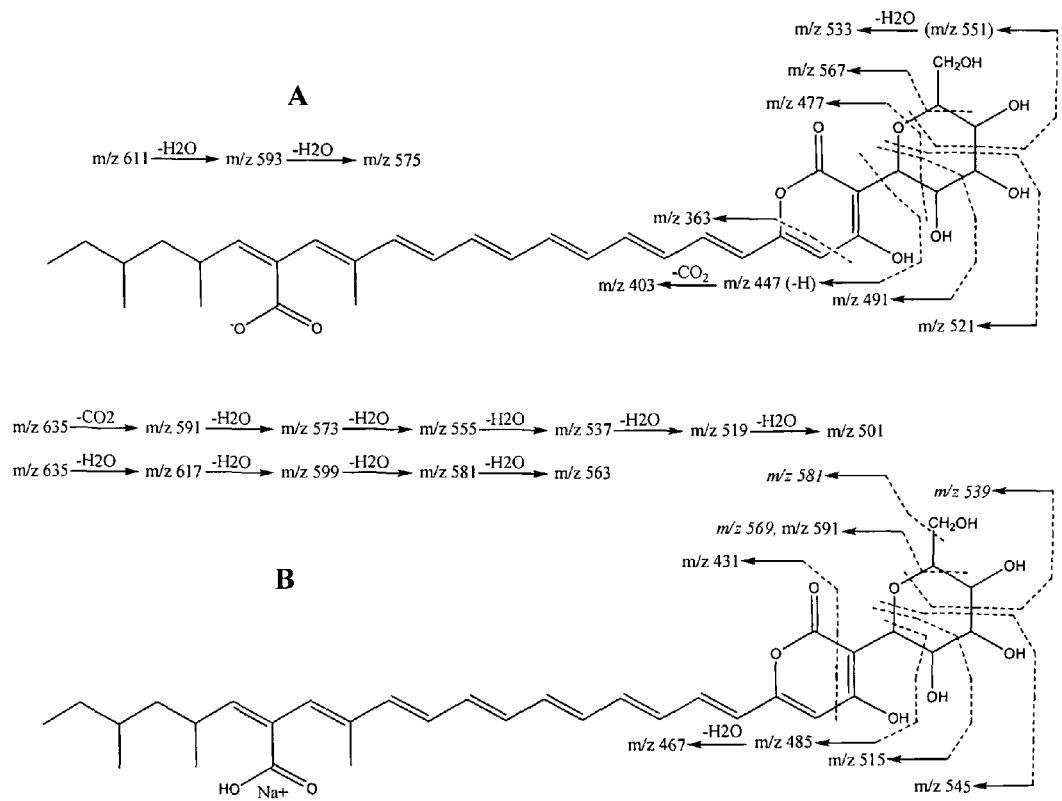
FIGURE 5A,B

ANTI-MICROBIAL COMPOSITIONS

STATEMENT OF CORRESPONDING APPLICATIONS

This application claims priority to U.S. Provisional Patent Application Ser. No. 61/376,402, filed Aug. 24, 2010, the entire disclosure of which is incorporated herein by reference.

TECHNICAL FIELD

The present invention relates generally to anti-microbial compositions. Particularly, although not exclusively, the present invention relates to a fungal exudate isolated from the filamentous fungal strain *Epicoccum purpurascens* (syn. *Epicoccum nigrum*) for use as a natural fungicide.

BACKGROUND ART

Fungi can cause serious damage to growing or harvested crops, particularly fruit or vegetable crops. Fungicides are also used to treat fungal infections in animals.

Traditionally the principle method of control of fungi growth has been the use of synthetically produced fungicide chemicals. These synthetic fungicides frequently have high toxicity to humans and to other organisms. Because of this the use of synthetic fungicides has become more restricted due to public concern of their toxicity.

The use of naturally occurring fungicides as an alternative to synthetic chemicals is becoming more attractive due to improved biodegradation and therefore the potential for lower toxicity to both the environment and consumers of the harvested crops.

*Epicoccum purpurascens* (syn. *E. nigrum*) is a saprophytic filamentous fungi usually associated with senescing plant tissues and soil. It produces high concentrations of secondary products including a pigment that gives the media it is grown on a yellow/orange (pH dependent) colour. An orange pigment, named orevactaene was isolated from *E. purpurascens* and its structure described (Shu, Y. Z., et al., Bioorganic & Medicinal Chemistry Letters, 1997 7(17): p. 2295-2298; see FIG. 1). Orevactaene was found to inhibit binding of HIV-1 regulatory protein and its viral RNA binding site. It was found to have modest antifungal activity against *Candidia albacans* (MIC 250 µg/mL). The structure of orevactaene was determined to be that shown in FIG. 1.

Several fungal metabolites were also isolated from *E. purpurascens* by Kemami Wangun as described in a 2006 dissertation [Kemami Wangun, H., V, 2006, Friedrich-Schiller: University of Jena]. A yellow oil was isolated and was identified as orevactaene.

Other biologically active compounds secreted by other *E. purpurascens* strains have been characterised including flavipin which demonstrated antimicrobial activity against bacteria and fungi (Brown A E. et al., Soil Boil. 1987 Biochem. 19: 657-664 and Burge W R. et al., 1976 J. Agric. Food Chem. 24: 555-559), and epicoccamides (Wangun H V K. et al., 2007 J. Nat. Prod. 70: 1800-1803; Wright A D. et al., 2003 Org. Biomol. Chem. 1: 507-510) and thiornicin (Frederick C B. et al., 1981 Biochem. 20: 2436-2438) which has been demonstrated as having anti-cancer activity.

The potential use of *E. purpurascens* strains as a biological control for fungal growth on crops has been reported (Bhuiyan S A. et al., 2003 Plant Path. 52: 60-67; Mari M. et al., 2007 J. Sci. Food Agric. 87: 1271-1277; Szandala E S and Backhouse D 2001 Aust. Plant Path. 30: 165-170), however no demonstration of an effective control agent has been shown largely due to unsatisfactory growth and activity of the *E. purpurascens* strains under environmental conditions.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF INVENTION

According to another aspect of the present invention there is provided an agricultural composition comprising:
  an agriculturally acceptable carrier; and
  an anti-microbial compound of formula (I):

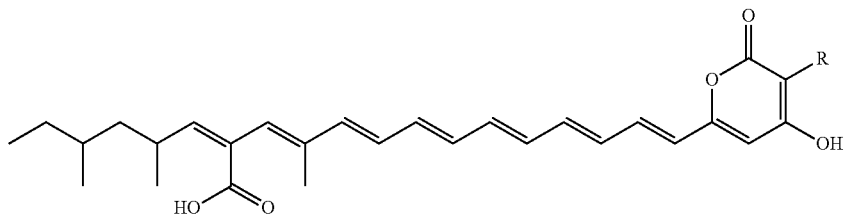

wherein
  R is selected from the group consisting of:
    C-β-D-galactopyranose; C-α-D-galactofuranose; C-β-D-galactofuranose; galactopyranose; C-α-L-galactofuranose; C-β-L-galactofuranose; or related pyranose; and a salt, derivative, tautomer, stereoisomer, hydrate, solvate or sugar analogue thereof.

According to another aspect of the present invention there is provided a pharmaceutical composition comprising:
a pharmaceutically acceptable carrier or diluents; and
an anti-microbial compound of formula (I):

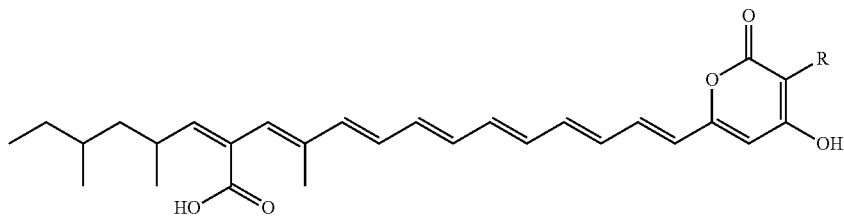

wherein
R is selected from the group consisting of:
C-β-D-galactopyranose; C-α-D-galactofuranose; C-β-D-galactofuranose; C—β-L-galactopyranose; C-α-L-galactofuranose; C-β-L-galactofuranose; or related pyranose; and
a salt, derivative, tautomer, stereoisomer, hydrate, solvate, sugar analogue, pro drug thereof.

Preferably, the composition is in the form of a powder.

According to another aspect of the present invention there is provided the use of a compound formula (I):

wherein
R is selected from the group consisting of:
C-β-D-galactopyranose; C-α-D-galactofuranose; C-β-D-galactofuranose; C-β-L-galactopyranose; C-α-L-galactofuranose; C-β-L-galactofuranose; or related pyranose; and
a salt, derivative, tautomer, stereoisomer, hydrate, solvate or sugar analogue thereof in the manufacture of a composition for the treatment of a microbial infection in a plant or a plant part thereof.

Preferably, the microbial infection is a fungal infection.

Preferably, the plant part is a fruit crop plant or a vegetable crop plant.

According to another aspect of the present invention there is provided the use of a compound formula (I):

wherein
R is selected from the group consisting of:
C-β-D-galactopyranose; C-α-D-galactofuranose; C-β-D-galactofuranose; C-β-L-galactopyranose; C-α-L-galactofuranose; C-3-L-galactofuranose; or related pyranose; and
a salt, derivative, tautomer, stereoisomer, hydrate, solvate, sugar analogue or pro-drug thereof in the manufacture of a medicament for the treatment of microbial infection in an animal or a animal part thereof.

Preferably, the animal is a human.

According to another aspect of the present invention there is provided a method of preventing, removing or inhibiting a microbial infection in a plant or plant part thereof, comprising the step:

applying to the plant or plant part thereof a treatment effective amount of a composition comprising:
a compound of formula (I):

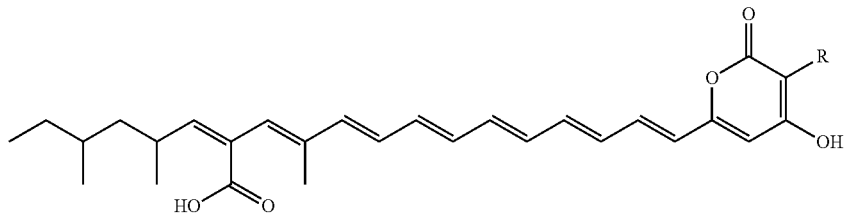

wherein
R is selected from the group consisting of:
C-β-D-galactopyranose; C-α-D-galactofuranose; C-β-D-galactofuranose; C-β-L-galactopyranose; C-α-L-galactofuranose; C-β-L-galactofuranose; or related pyranose; and
an agriculturally acceptable salt, derivative, tautomer, stereoisomer, hydrate, solvate or sugar analogue thereof.
Preferably, the method also comprises the step of:
applying to the plant or plant part thereof a treatment effective amount of the composition to prevent or inhibit the growth of *Botrytis* or *Lecanicillium*.
Preferably, the plant part is a fruit or a vegetable.
A method of preventing, treating or ameliorating a microbial infection to a subject in need of such prevention, treatment or amelioration.
Preferably, the subject is a non-human animal subject.
Preferably, the administration comprises topically administering the composition.

BRIEF DESCRIPTION OF DRAWINGS

Further aspects of the present invention will become apparent from the following description which is given by way of example only and with reference to the accompanying drawings in which:
FIG. 2A shows the chemical structure of the active ingredient of the present invention in the form of epipyrone A;
FIG. 2B shows the chemical structure of compounds related to that shown in FIG. 1 in the form of epipyrone B and epipyrone C;
FIG. 3A shows a mass spectrum for negative ion used in the elucidation of the chemical structure of the compound shown in FIG. 1;
FIG. 3B shows a mass spectrum for positive ion used in the elucidation of the chemical structure of the compound shown in FIG. 1;
FIG. 4A shows a Collision Induced Dissociation (CID) for negative ion used in the elucidation of the chemical structure of the compound shown in FIG. 1;
FIG. 4B shows a Collision Induced Dissociation (CID) spectrum for positive ion used in the elucidation of the compound shown in FIG. 1;
FIG. 5A shows a positive ion fragmentation pathway of used in the elucidation of the chemical structure of the compound shown in FIG. 1;
FIG. 5B shows a negative ion fragmentation pathway of used in the elucidation of the chemical structure of the compound shown in FIG. 1.

BEST MODES FOR CARRYING OUT THE INVENTION

Figure 1:
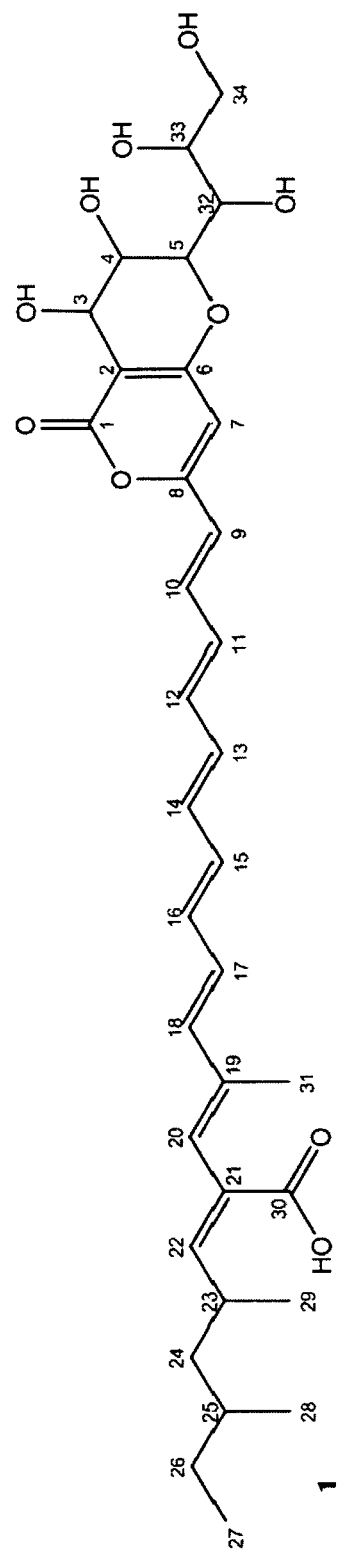
FIG. 1 shows the chemical structure of known compound orevactaene.

Extraction and Identification of the Active Ingredient:
Experiment 1
A high performance liquid chromatography (HPLC) method with diode array detection was setup to monitor pigment during purification. The same HPLC method was used for liquid chromatography mass spectroscopy (LCMS) analysis.
Four liters of *Epicoccum purpurascens* culture was prepared. The culture was centrifuged to separate the mycelium from the aqueous supernatant. HPLC analysis showed 90% of epipyrone A (as shown in FIG. 2A) was present in the mycelium, and therefore the aqueous supernatant was discarded. The 600 g of mycelium was freeze dried to afford 59 g of a brown powder. The brown powder was extracted several times with methanol yielding 11.6 g of red oil. The red oil was dissolved in 200 mL 0.1% sodium borate (pH 9) and extracted twice with 200 mL of ethyl acetate to remove neutral and basic compounds. All fractions were checked by HPLC, no epipyrone A had extracted into the ethyl acetate layer.
The aqueous layer was acidified with 85% phosphoric acid to pH 3 and epipyrone A was extracted with 200 mL of ethyl acetate. A little ethanol was added to facilitate separation of the two layers. The ethyl acetate was removed by rotary evaporation and the weight of the dried residue was 1.6 g. The residue was dissolved in 40 mL of water containing 100 μL 25% NH4OH.
A column packed with Strata X polymeric resin 110 mm×38 mm was conditioned with methanol, followed by 60% acetonitrile (adjusted to pH 2.5 with dilution H3PO4)

and 30% acetonitrile (pH 2.5). 2 mL of the 40 mL extract containing epipyrone A was diluted with 18 mL of 30% acetonitrile (pH 2.5) and loaded onto the column. The column was eluted with vacuum using the following step gradient:

200 mL 30% acetonitrile (pH 2.5)
200 mL 40% acetonitrile (pH 2.5)
500 mL 50% acetonitrile (pH 2.5)
700 mL 55% acetonitrile (pH 2.5)

Fractions were collected once the orange band started to elute, this began with 55% acetonitrile (pH 2.5). In total five fractions were collected. Ethyl acetate was added to each of the five fractions and the orange pigment moved to the ethyl acetate layer. HPLC analysis revealed that 75% of epipyrone A (ca 9.6 mg) was in the first two fractions, these were combined and dried.

A 1 g Strata Si-1 SPE column was conditioned with 10 mL chloroform. The dried residue (containing approximately 9.6 mg epipyrone) was dissolved in 5 mL of 5:95 methanol/chloroform and was loaded onto to the silica column. The column eluted with 5:95 methanol/chloroform followed by 10:90 methanol/chloroform. A total of nine fractions were collected and analysed by HPLC. Fractions 6 and 7 were combined and dried on $N_2$ blowdown. The residue was dissolved in 50% methanol and loaded onto a 1 g Strata X SPE column. The column washed with 20 mL 3:7 methanol/water to remove silica fines and epipyrone A was eluted with 15 mL methanol. The methanol was removed on $N_2$ blowdown and the residue was placed under high vacuum on free dryer for 48 hrs to remove residual solvent. The residue weighed 5.4 mg.

Assessment of Purity

HPLC analysis during the purification of epipyrone A revealed the presence of at least two closely related compounds epipyrone B and epipyrone C (as shown in FIG. 2B). Further analysis showed these compounds shared the same molecular weight, UV absorbance and the similar MS/MS fragmentation. During the final stages of purification separation of epipyrone B and epipyrone C from epipyrone A was achieved, however it was quickly discovered that these compounds were in inter-convertible. Regardless of the starting composition (epipyrone A:epipyrone B+epipyrone C), the final composition of the mixture ended up as 70% of epipyrone A and 30% of epipyrone B+epipyrone C. This interconversion appears to be acid catalysed. epipyrone B and epipyrone C were also present in the *E. purpurascens* culture and therefore is not an artifact of the purification process.

The mixture of epipyrone A, epipyrone B and epipyrone C had a ratio of about 100:25:7 and found to be >95% pure by high performance liquid chromatography with diode array (HPLCDAD), liquid chromatography with mass spectroscopy (LC-MS) and nuclear magnetic resonance (NMR).

Compounds epipyrone B and epipyrone C are α- and β-furanoside isomers.

Extraction and Identification of the Active Ingredient: Experiment 2

Ethanol Extraction

Figure 8:
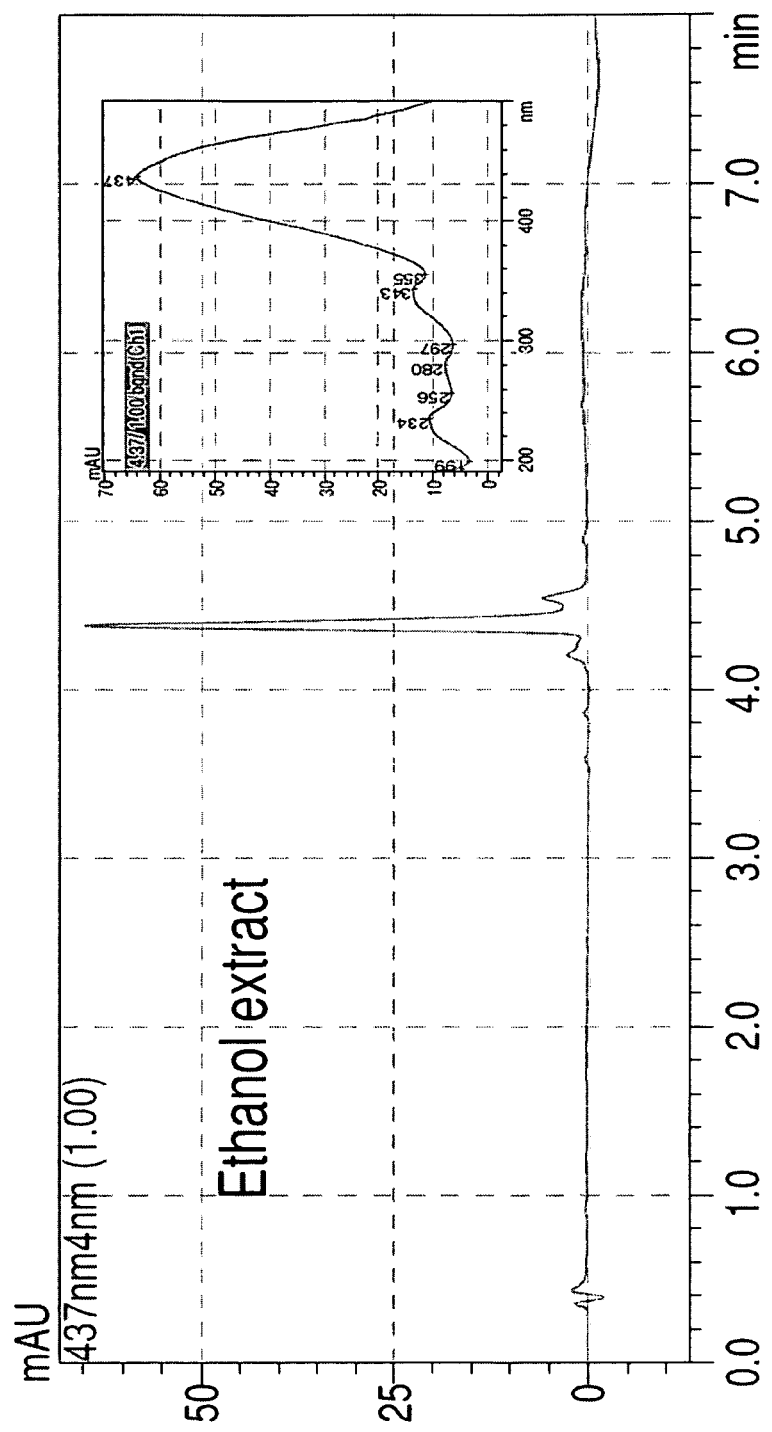
FIG. 8 shows a chromatogram and UV spectrum scan of an ethanol extract of a culture of *Epicoccum purpurascens* (syn. *E. nigrum* strain SF7489) using HPLC method 1.
Figure 9:
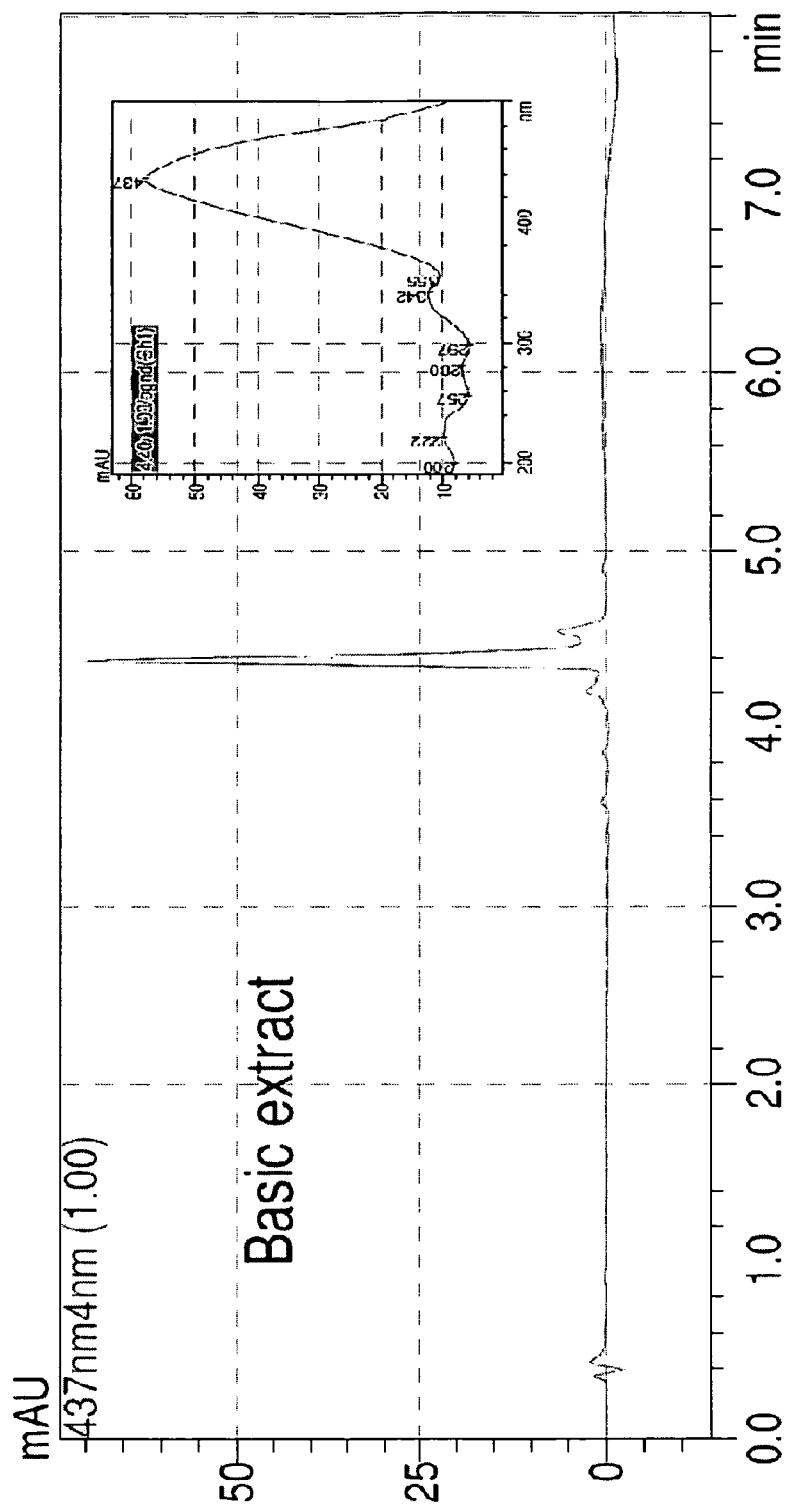
FIG. 9 shows a chromatogram and UV spectrum scan of the ethanol extract and the culture of FIG. 8 using HPLC method 2.

A culture of *Epiccocum nigrum* strain SF7489 was centrifuged at 3000 g for 10 min to separate the mycelium from the liquid broth. The mycelium (1200 g) was extracted twice with a total of 1.2 L ethanol by homogenizing with a hand held blender. The solid was removed by centrifugation and the ethanolic supernatant was retained. Both the liquid broth that was originally separated from the mycelium and the mycelium ethanol extract were analysed by HPLC to identify and measure the concentrations of the yellow pigment using two different HPLC methods 1 and 2 as below for comparison (results shown in FIG. 8 and FIG. 9 respectively).

About 15% of the yellow pigment was in liquid culture broth. The liquid broth was combined with the ethanol extract to give 3.6 L of extract. A 10 fold dilution of this sample was prepared for HPLC analysis. The ethanol extract was split in two equal portions. One portion was to be extracted and quantified using method 1 and one portion using method 2.

HPLC Method 1:

Mobile phase A—0.1% acetic acid; mobile phase B—Acetonitrile; column—Ascentis C8 Express 2.7 µm 50×2.1 mm; flow—0.5 mL/min; Injection volume—1 µl; column oven—15° C.; gradient—30% B to 70% B over 5 min, then returned to 30% over 1 min and re-equilibrated for 2 mins; Detector—Photodiode array scan 250-500 nm extract chromatogram at 437 nm.

An extinction co-efficient that was established from pure epipyrone was used on method 1 to quantify the concentration of compound in the various samples.

HPLC Method 2:

Mobile phase A—$NH_4OH$ in water pH10; Mobile phase B—1:4 isopropanol/methanol; column—Phenomenex Gemini C18 5 µm 150×2 mm; Flow—0.2 mL/min; injection volume—1 µL; column oven—15° C.; gradient—25% B to 100% B over 12 min, held for 1 min, then returned to initial conditions over; 2 mins and re-equilibrated for 5 mins; detector—Photodiode array scan 190-500 nm extract chromatogram at 428 nm.

Because we did not have an extinction co-efficient for method 2 we just looked at relative peak areas.

Acid Extraction

Figure 10:
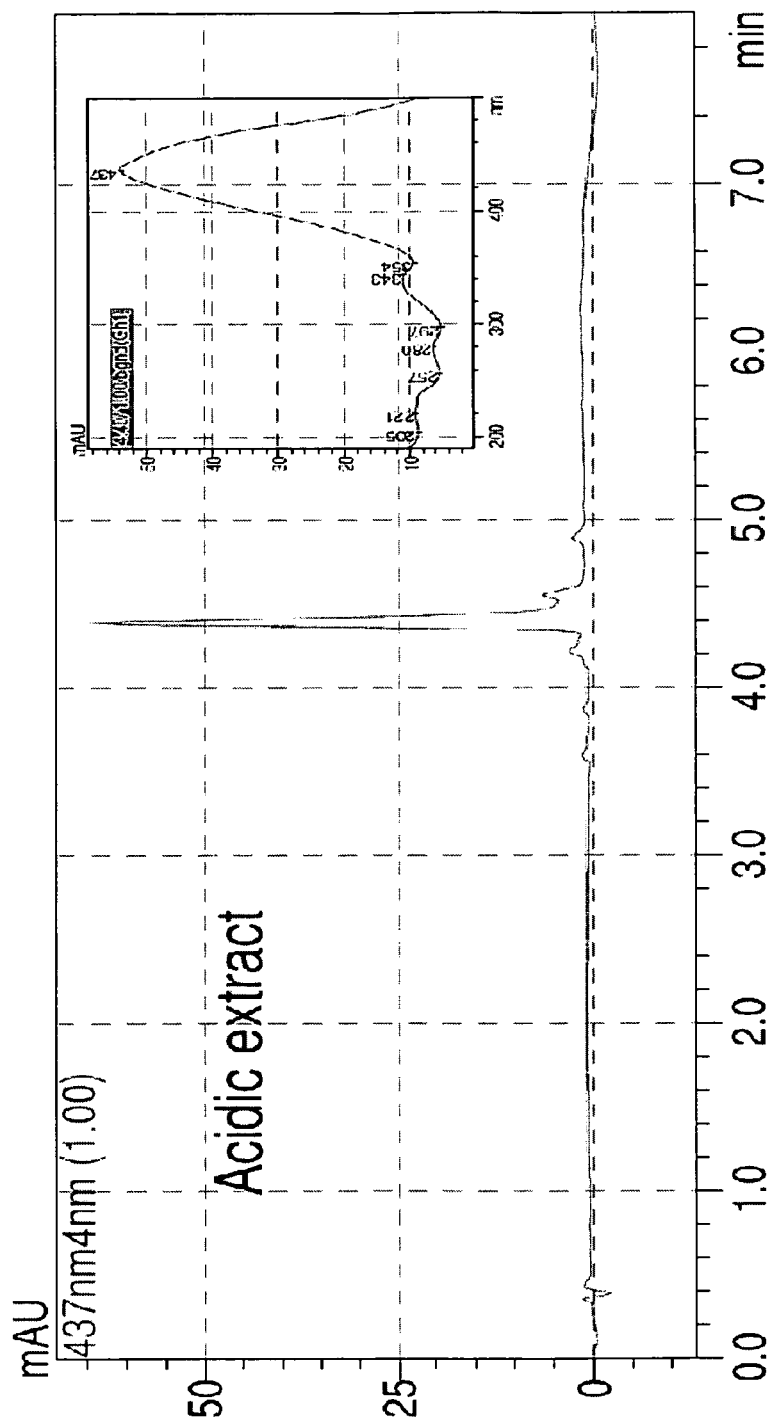
FIG. 10 shows a chromatogram and UV spectrum scan of a basic extract of the culture of FIG. 8 using HPLC method 1.
Figure 11:
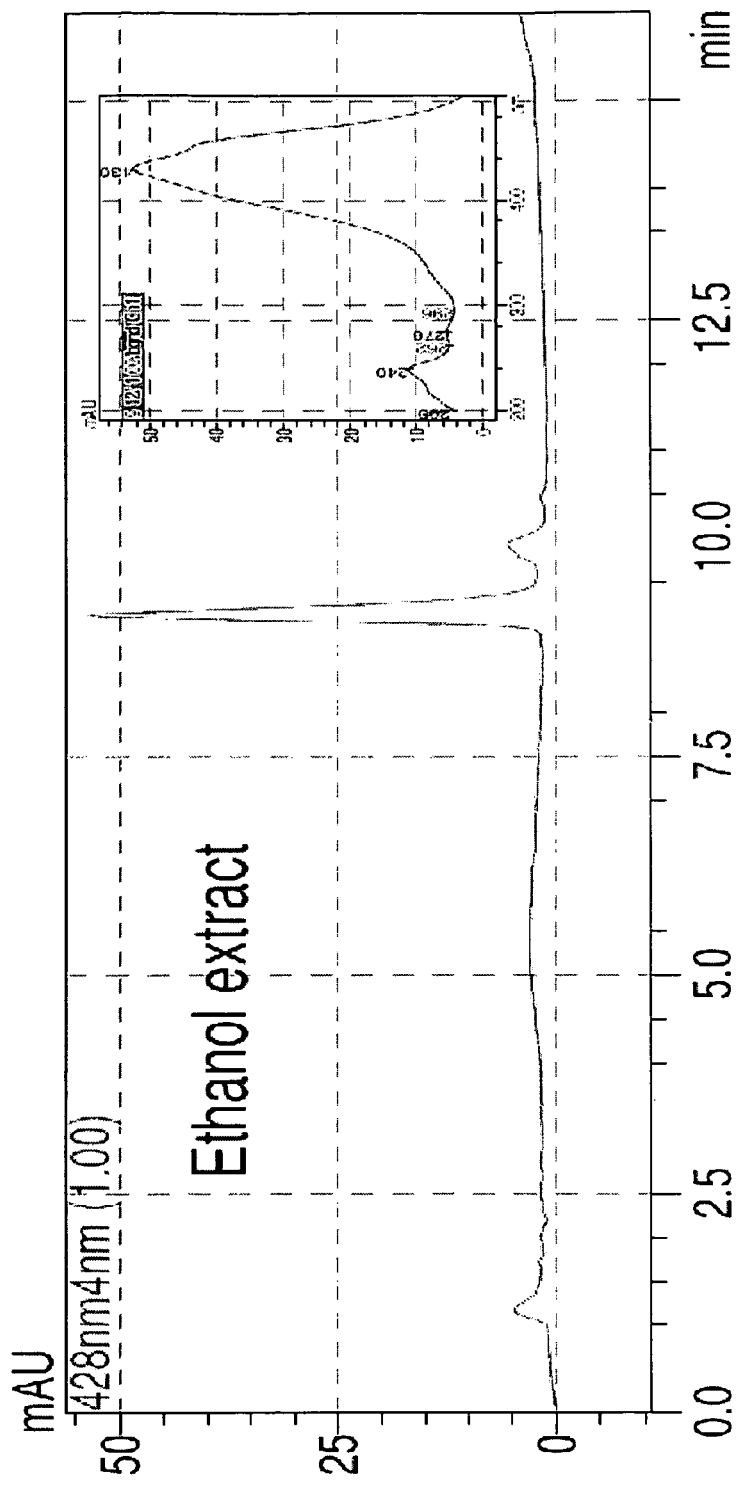
FIG. 11 shows a chromatogram and UV spectrum scan of a basic extract of the culture of FIG. 8 using HPLC method 2.

The volume of the extract was reduced by rotary evaporation to 0.8 L. This was then acidified to pH 2.5 with phosphoric acid. The addition of the acid precipitated the pigment as the protonated compound is not water soluble. The acidified solution was then centrifuged at 3000 g for 10 min. The supernatant was tested by HPLC method 1 (result shown in FIG. 10) and HPLC method 2 (result shown in FIG. 10) and was found to contain about 10 mg of the pigment. The solid was redissolved in 80 mL of pH 7.4 50 mM phosphate buffer. A 200 fold dilution of this sample was prepared for HPLC analysis. The remainder of the sample was stored at −20° C.

Base Extraction

Figure 12:
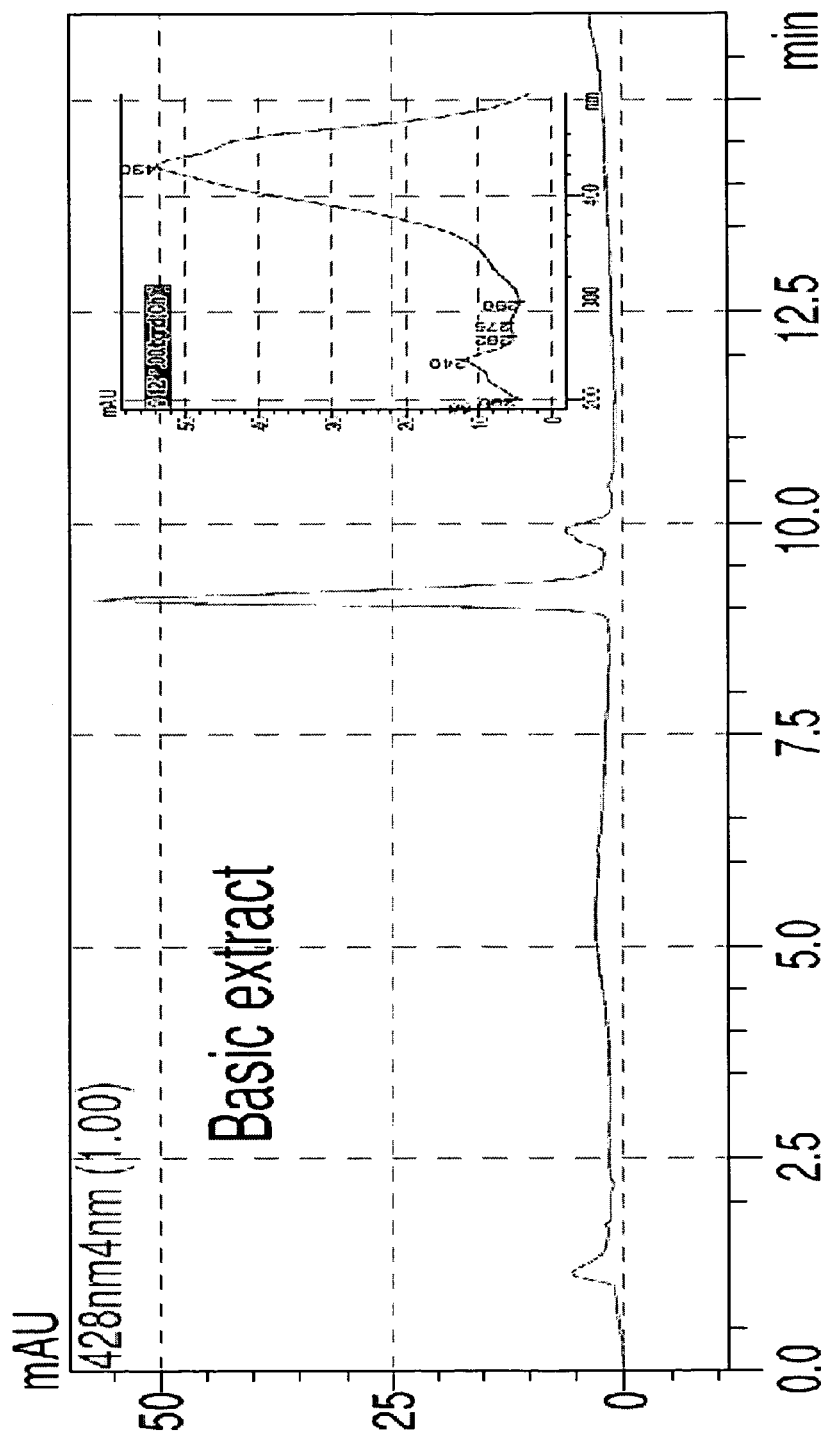
FIG. 12 shows a chromatogram and UV spectrum scan of a acidic extract of the culture of FIG. 8 using HPLC method 1.
Figure 13:
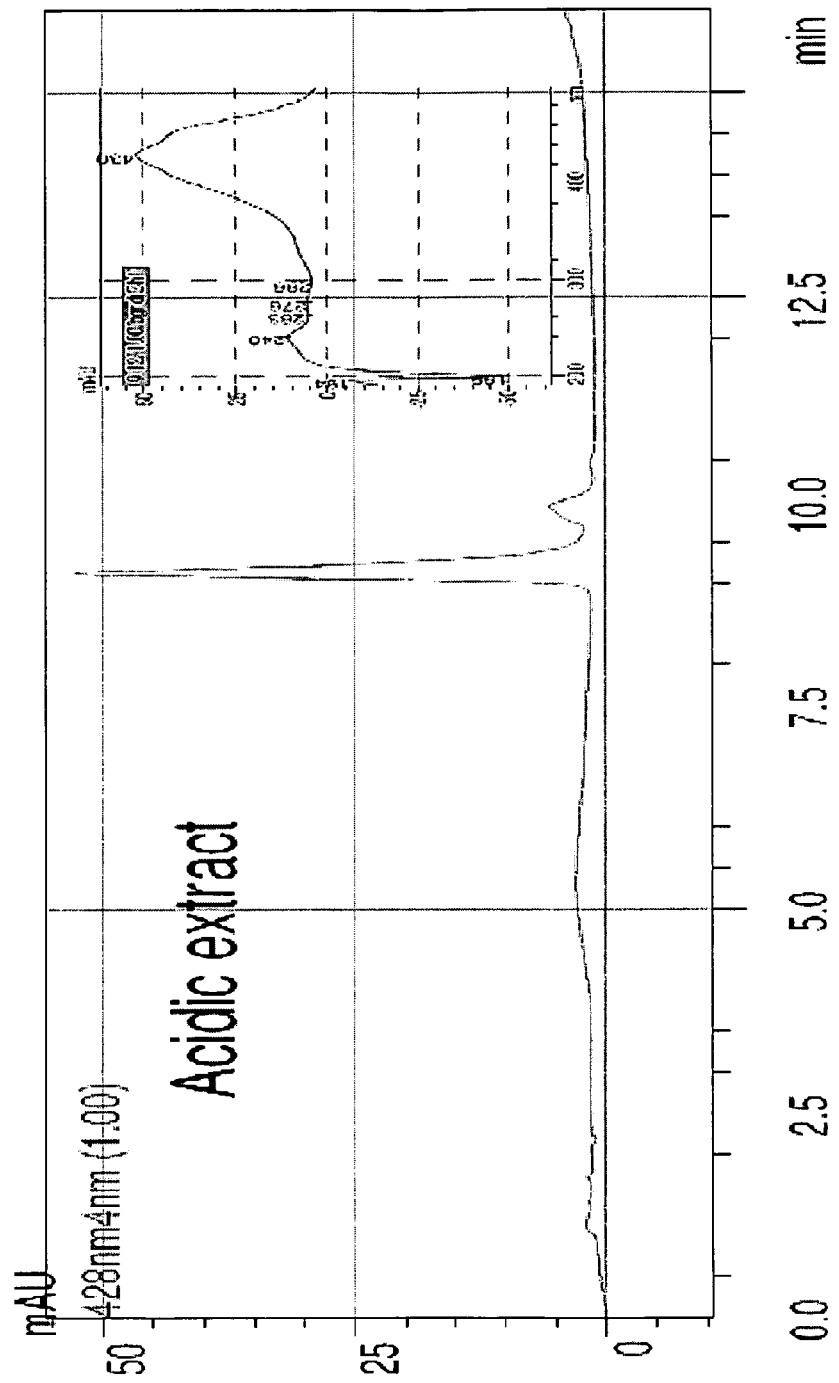
FIG. 13 shows a chromatogram and UV spectrum scan of a acidic extract of the culture of FIG. 8 using HPLC method 2.

The pH of the other portion of the extract was adjusted to pH10 with $NH_4OH$ and evaporated to dryness by rotary evaporation. This sample was dissolved in 80 mL pH 7.4 50 mM phosphate buffer. A 200 fold dilution of this sample was prepared for HPLC analysis (HPLC method 1 results shown in FIG. 12 and HPLC method 2 results shown in FIG. 13). The remainder of the sample was stored at −20° C.

Dry Weight of Culture Solids

The ethanol extracted mycelium was dried at room temperature overnight then dried further in an oven at 100° C. for 3 hours to remove residual solvent. The weight of the dried mycelium was 16 g. The ethanol extract from the base extraction was weighed after rotary evaporation, the extract weighed 13 g. This was extract was only half of the total extract, therefore the total weight of solids in the broth+ethanol extract was 26 g. The total weight of solid from 2.5 L of culture was 42 g which works out to be 16.8 g of solids per liter of culture. The total weight of the pure yellow pigment called epipyrone or epicoccane or orevactaene extracted from 2.5 L of culture was 250 mg, this is equivalent to 100 mg/L, this is consistant with yields from previous extraction.

This means that the approximate concentration of epipyrone is 0.01% in the liquid culture or 0.6% of the dry weight.

CONCLUSION

Analysis by both HPLC methods found that the yellow pigment in the original ethanol extract and in both of the acid and base sample extracts shared identical chromatographic and spectral properties. Both extractions yielded the same amount of this pigment (120 mg and 130 mg). Therefore we conclude that the extraction method is not critical as both methods yielded the same compound and the same amount of compound.

This result is similar to the concentrations of a similar pigment, beta carotene, in carrots. The concentration of beta carotene in fresh carrots is approximately 0.0008% and 0.1% of dry weight. The concentration of _-carotene was sourced from Wikipedia http://en.wikipedia.org/wiki/Carrots and the water content of carrots was sourced from the University of Kentucky http://www.ca.uky.edu/enri/pubs/enri129.pdf.

Structural Elucidation of the Active Ingredient

NMR Spectroscopy

For NMR analysis the purified sample as described above was dissolved in CD3OD.

The structures of 3,5,7,9,11,13-Tetradecahexaenoic acid, 2-(2,4-dimethylhexylidene)-14-(3-β-D-galactopyranosyl-4-hydroxy-2-oxo-2H-pyran-6-yl)-4-methyl (epipyrone A), 3,5, 7,9,11,13-Tetradecahexaenoic acid, 2-(2,4-dimethylhexylidene)-14-(3-α-D-galactofuranosyl-4-hydroxy-2-oxo-2H-pyran-6-yl)-4-methyl (epipyrone B) and 3,5,7,9,11,13-Tetradecahexaenoic acid, 2-(2,4-dimethylhexylidene)-14-(3-β-D-galactofuranosyl-4-hydroxy-2-oxo-2H-pyran-6-yl)-4-methyl (epipyrone C) were elucidated using 1H, 13C, distortionless enhancement by polarization transfer (135DEPT), heteronuclear single quantum correlation (HSQC), heteronuclear multiple bond correlation (HMBC), correlation spectroscopy (COSY), total correlation spectroscopy (TOCSY), rotating frame overhauser effect spectroscopy (ROESY), nuclear overhauser effect spectroscopy (NOESY), selective total correlation spectroscopy (SELTOCSY) and selective rotating frame overhauser effect spectroscopy (SELROESY) experiments. NMR data are presented in Table 1 below.

TABLE 1

$^1$H and $^{13}$C NMR data for 3 in CD$_3$OD.

| $^{13}$C | $^1$H | mult | J (Hz) | comments |
|---|---|---|---|---|
| 1 | 171.1 | | | |
| 2 | 101.5 | | | overlapped with C4 |
| 3 | 166.2 | | | |
| 4 | 102.4 | 6.07 | s | overlapped with C2 |
| 5 | 160.0 | | | |
| 6 | 122.5 | 6.19 | d | 15.1 |
| 7 | 137.5 | 7.13 | dd | 15.1, 11.4 |
| 8 | 132.0 | 6.45 | | |
| 9 | 140.5 | 6.63 | dd | 14.6, 11.0 overlapped with C15 |
| 10 | 130.2 | 6.40 | | |
| 11 | 138.2 | 6.5 | | |
| 12 | 134.0 | 6.4 | | |
| 13 | 137.0 | 6.42 | | |
| 14 | 132.4 | 6.42 | | |
| 15 | 140.5 | 6.4 | | overlapped with C9 |
| 16 | 137.5 | | | |
| 17 | 131.5 | 6.12 | s | |
| 18 | 132.0 | | | |
| 19 | 149.0 | 5.58 | d | 10.3 |
| 20 | 33.3 | 3.01 | | |
| 21 | 46.1 | 1.11, 1.36 | | |
| 22 | 34.0 | 1.32 | | |
| 23 | 31.4 | 1.17, 1.32 | | |
| 24 | 11.8 | 0.87 | | |
| 25 | 19.5 | 0.86 | | |
| 26 | 22.0 | 1.02 | | |
| 27 | 172.3 | | | |
| 28 | 14.0 | 1.88 | | |
| 1' | 76.7 | 4.54 | d | 9.7 |
| 2' | 70.5 | 4.21 | dd | 9.5 appears as triplet |
| 3' | 76.8 | 3.52 | dd | 9.4, 3.2 |
| 4' | 71.3 | 3.92 | d | 3.2 broad doublet |
| 5' | 81.0 | 3.61 | m | |
| 6' | 62.9 | 3.72 | m | |

The chemical shifts in CD3OD for epipyrone A were similar to those stated by Shu et al for orevactaene in DMSO-d6. Some of the 1H chemical shifts were significantly different, this is explained by the solvent used for analysis (CD3OD vs DMSO-d6).

The HMBC spectrum shows connectivities between Ht and C1, C2, C3, C2', C3' and C5'. The correlation between H1' and C5' shows that the two atoms are within 2-3 bond lengths. The chemical shifts of the C1' to C6' are consistent with a single oxygen linkage for each carbon and therefore C1' and C5' are most likely connected by and ether linkage. These observations showed that the pyranoside residue was linked to C2 on the pyrone ring via C-rather than an O-pyranoside linkage.

Large H1'-H2' and H2'-H3' coupling constants of the order 9-10 Hz are consistent with the proposed pyranoside structure. 1D-selective ROESY experiments show correlations between H1' and H3', H1 and H5' as well as H3' and H5'. 1D-SELTOCSY experiments with different mixing times was used to confirm the chemical shifts and correlation pathways of H1' through to H6'. In combination these experiments showed the pyranose ring is in the preferred chair confirmation and the 4'-OH is axially orientated while the H1'-H-2' coupling (J=9.7 Hz) shows that the C-pyranose unit is beta linked to the pyrone. These findings led to the identification of structure of epipyrone A as a β-C-D-galactopyranoside.

Structures could also be assigned to the two minor isomers epipyrone B and epipyrone C present in the same sample. Based on HMBC and ROESY correlations they were found to be α- and β-anomers of C-D-galactofuranosides rather than the pyranoside compound epipyrone A (see Table 2).

TABLE 2

$^1$H and $^{13}$C NMR data for C-glycoside moiety for 3, 4 and 5 in CD$_3$OD.

| | 3 | | | 4 | | | 5 | | |
|---|---|---|---|---|---|---|---|---|---|
| | $^{13}$C | $^1$H | mult, J = Hz | $^{13}$C | $^1$H | mult, J = Hz | $^{13}$C | $^1$H | mult, J = Hz |
| 1' | 76.7 | 4.54 | d 9.7 | 83.1 | 5.23 | d 3.2 | 79.3 | 5.10 | d, 7.1 |
| 2' | 70.5 | 4.21 | dd 9.5, 9.5 | 79.0 | 4.15 | dd 3.2, 1.5 | 80.2 | 4.61 | dd 7.1, 5.9 |
| 3' | 76.8 | 3.52 | dd 9.4, 3.2 | 80.9 | 4.20 | m | * | 4.18 | m |

TABLE 2-continued $^1$H and $^{13}$C NMR data for C-glycoside moiety for 3, 4 and 5 in CD$_3$OD.

| | 3 | | | 4 | | | 5 | | |
|---|---|---|---|---|---|---|---|---|---|
| | $^{13}$C | $^1$H | mult, J = Hz | $^{13}$C | $^1$H | mult, J = Hz | $^{13}$C | $^1$H | mult, J = Hz |
| 4' | 71.3 | 3.92 | br d 3.2 | 87.5 | 4.01 | dd 2.4, 3.0 | 84.4 | 4.04 | dd 6.6, 3.5 |
| 5' | 81.0 | 3.61 | m | 72.8 | 3.88 | ddd 6.4, 6.4, 3.0 | 72.9 | 3.75 | m |
| 6' | 62.9 | 3.72 | m | 63.6 | 3.62 | m | 62.4 | 3.71 | m |

\* Concealed

Mass Spectrometry

In negative ion mode a strong [M–H]– m/z 611.3 molecular ion was observed with a small loss of CO2 (44 amu) m/z 567.3 peak (FIG. 3A). In positive ion mode an [M+H]+ m/z 613.3 and a [M+Na]+ m/z 635.3 were the predominant molecular ions observed (FIG. 3B).

Collision-induced dissociation (CID) experiments in negative ion mode revealed the prominent fragments m/z 403, 447, 491 and 521 (FIG. 4A) and in positive ion a series of water losses and m/z 569, 545, 539, 515 and 485 (FIG. 4B). The proposed fragmentation pathways of epipyrone A in both positive and negative ion mode are shown in FIG. 5. The proposed fragmentation pathway shows that the pyrone ring is intact and is consistent with the proposed structure of epipyrone A.

Micro-Scale Reaction Chemistry

Acetylation Experiment

A subsample of compound epipyrone A was dissolved in mixture of dry 900 μL dichloromethane, 50 μL acetic anhydride and 50 μL pyridine. The reaction was monitored by LC-MS positive ion scanning. Analysis of the sample showed a mixture of acetylated compounds with the addition of 2 to 5 acetates indicating the presence of at least five hydroxyls. This is consistent with the proposed structure of epipyrone A (FIG. 5).

Methylation Experiment

Figure 6:
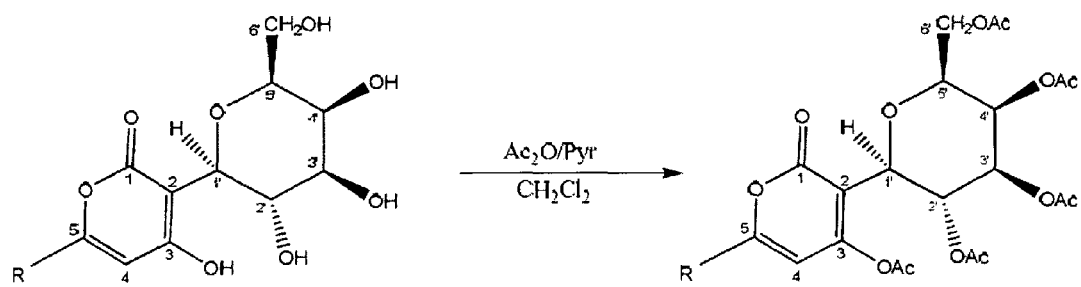
FIG. 6 shows a reaction scheme for the acetylation of the hydroxyls which is used in the elucidation of the chemical structure of the compound shown in FIG. 1.
Figure 7:
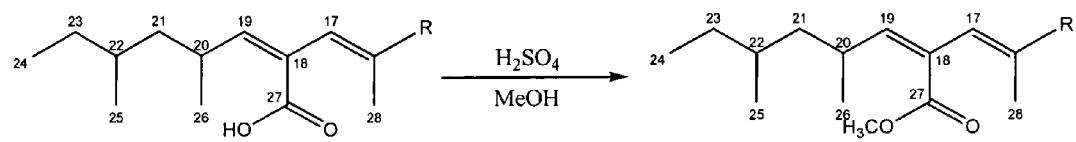
FIG. 7 shows a reaction scheme for the acetylation of the hydroxyls which is used in the elucidation of the compound shown in FIG. 1.

A subsample of compound epipyrone A was dissolved in 200 μL of MeOH+5 μL of H2SO4. The reaction was monitored by LC-MS positive ion scanning. Esterfication was slow at room temperature so the sample was heated to 50° C. for 2 hours resulting in 60% conversion to a single methyl ester. This indicates that one carboxylic is present and is consistent with the proposed structure of epipyrone A (FIG. 6).

For the purposes of the specification the preferred embodiment of the structure of compound epipyrone A 4-hydroxy-6-(11',15',17'-trimethyl-13'-carboxy-nonadeca-1',3',5',7',9',11',13'-heptene)-2-pyrone-1-C-galactopyranoside was called epipyrone A.

Biological Activity Demonstration: *Epicoccum nigrum* Extract Challenge Test

Materials

A sample of *Epiccocum purpurascens* (syn. *nigrum* strain SF7489) was prepared by extracting 1 L of culture with 1 L of ethanol, then the solids were removed by filtration and the liquid was removed by rotary evaporation. The residue was resuspended in 25 mL of water. A sub-sample was diluted and analysed by HPLC to determine the concentration of Epipyrone. The Epipyrone concentration was measured to be 3.4 mg/mL.

The 25 mL solution was aliquoted into 5 vials and frozen.

Method

*Botrytis cinerea* strain ICMP 16221 was grown on PDA (potato dextrose agar) to obtain spores. *Lecanicillium muscarium* K4V1 was grown on SA (Sabourard Agar) to obtain spores. Epipyrone was introduced into 2 mL spore solutions of the *B. cinerea* and *L. muscarium* at the following concentrations in sterilised test tubes then incubated for 48 hrs at 26° C. Solutions were then examined under the microscope for signs of spore germination.

1. Control: Spore Solution no Epipyrone;
2. Net: Spore solutions mixed with undiluted extract concentration of Epipyrone (3.4 mg/mL=3400 mg/L);
3. Spore solution diluted to Epipyrone concentration 1000 mg/L;
4. Spore solution diluted to Epipyrone concentration 500 mg/L;
5. Spore solution diluted to Epipyrone concentration 250 mg/L; and
6. Spore solutions diluted to Epipyrone concentration 125 mg/L.

Results

The extent of spore growth in each of the 6 test tubes is shown in the table below:

| Sample | *Botrytis* Growth | *Lecanicillium* Growth | Comments |
|---|---|---|---|
| 1. Control | Good growth | Good Growth | Spores very viable: high germination rate and forming mycelium. |
| 2. 3.4 mg/mL epipyrone net extract | No growth | No growth | Spores globose distended and non viable (no germination) |
| 3. Extract 1000 mg/L epipyrone | No growth | No growth | Spores globose, distended and non viable |
| 4. Extract 500 mg/L epipyrone | No growth | No growth | Spores globose, distended and non viable |
| 5. Extract 250 mg/L epipyrone | No growth | No growth | Spores globose, distended and non viable |
| 6. Extract 125 mg/L epipyrone | Some growth | Some growth | Spores germinating to form mycelium. Spores and mycelium swollen and distended. Growth inhibited. |

CONCLUSION

Inhibition of spore growth was demonstrated with Epipyrone concentrations of greater than 250 mg/L.

Aspects of the present invention have been described by way of example only and it should be appreciated that modifications and additions may be made thereto without departing from the scope thereof as defined in the appended claims.

What we claim is:

1. A method of removing, inhibiting, treating or ameliorating a microbial infection, the method comprising the step of contacting one or more microbes with an effective amount of a compound of formula (I):

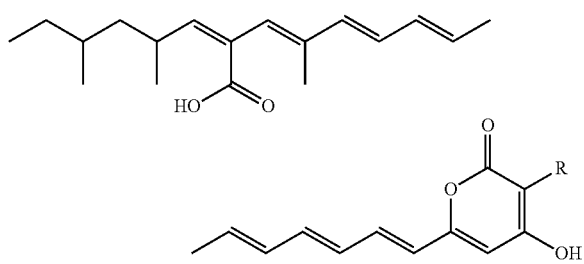

or a salt, tautomer, stereoisomer, hydrate, or solvate thereof, wherein

R is selected from the group consisting of C-β-D-galactopyranose; C-α-D-galactofuranose; C-β-D-galactofuranose; C-β-L-galactopyranose; C-α-L-galactofuranose; C-β-L-galactofuranose; or a related pyranose.

2. The method of removing or inhibiting a microbial infection according to claim 1, wherein the microbial infection is in a plant or plant part thereof, the method comprising the step of applying to the plant or plant part thereof a treatment effective amount of a compound of formula (I):

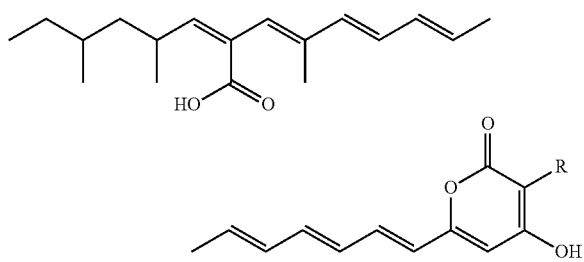

or a salt, tautomer, stereoisomer, hydrate, or solvate thereof, wherein

R is selected from the group consisting of C-β-D-galactopyranose; C-α-D-galactofuranose; C-β-D-galactofuranose; C-β-L-galactopyranose; C-α-L-galactofuranose; C-β-L-galactofuranose; or a related pyranose.

3. The method as claimed in claim 2 wherein the method also comprises the step of applying to the plant or plant part thereof a treatment effective amount of the compound to inhibit the growth of *Botrytis* or *Lecanicillium*.

4. The method as claimed in claim 2 wherein the plant part is a fruit or a vegetable.

5. The method of inhibiting, treating, or ameliorating a microbial infection according to claim 1, which comprises administering to a subject in need of such inhibition, treatment, or amelioration an effective amount of a compound of formula (I):

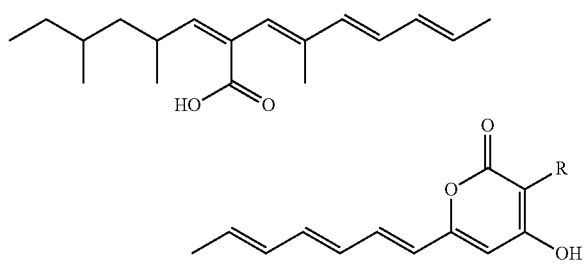

or a salt, tautomer, stereoisomer, hydrate, or solvate thereof, wherein

R is selected from the group consisting of C-β-D-galactopyranose; C-α-D-galactofuranose; C-β-D-galactofuranose; C-β-L-galactopyranose; C-α-L-galactofuranose; C-γ-L-galactofuranose; or a related pyranose.

6. The method as claimed in claim 5 wherein the subject is a non-human animal subject.

7. The method as claimed in claim 5 wherein the compound is administered as a composition additionally comprising a pharmaceutically acceptable carrier or diluent.

8. The method as claimed in claim 7 wherein the subject is a non-human animal subject.

9. The method as claimed in claim 7 wherein the administration comprises topically administering the composition.

10. The method as claimed in claim 5 wherein the administration comprises topically administering the compound.

11. The method as claimed in claim 5, wherein the compound of formula (I) is administered to the subject before the microbe infects the subject to thereby inhibit infection.

\* \* \* \* \*

UNITED STATES PATENT AND TRADEMARK OFFICE
CERTIFICATE OF CORRECTION

| | |
|---|---|
| PATENT NO. | : 8,889,636 B2 |
| APPLICATION NO. | : 13/216443 |
| DATED | : November 18, 2014 |
| INVENTOR(S) | : van Ginkel et al. |

It is certified that error appears in the above-identified patent and that said Letters Patent is hereby corrected as shown below:

On title page, item (60), replace "Aug. 27, 2010" with -- Aug. 24, 2010 --.

In the Claims

Column 14, line 28, claim 5, replace "C-y-L" with -- C-β-L --.

Signed and Sealed this
Second Day of June, 2015

Michelle K. Lee
*Director of the United States Patent and Trademark Office*